United States Patent [19]
Arvinte et al.

[11] Patent Number: 5,571,788
[45] Date of Patent: Nov. 5, 1996

[54] STABLE CALCITONIN PHARMACEUTICAL COMPOSITIONS

[75] Inventors: Tudor Arvinte, Billingshurst; Katherine D. Ryman, Guildford, both of Great Britain

[73] Assignee: Ciba-Geigy Corporation, Tarrytown, N.Y.

[21] Appl. No.: 185,757

[22] Filed: Jan. 24, 1994

Related U.S. Application Data

[63] Continuation of Ser. No. 73,646, Jun. 8, 1993, abandoned, which is a continuation of Ser. No. 805,252, Dec. 9, 1991, abandoned.

[51] Int. Cl.⁶ .................. A61K 38/00; A61K 38/02; A61K 38/30; C07K 5/00
[52] U.S. Cl. .................................. 514/12; 530/307
[58] Field of Search ................... 514/12; 530/307

[56] References Cited

U.S. PATENT DOCUMENTS

| | | | |
|---|---|---|---|
| 4,151,276 | 4/1979 | Caulin et al. | 424/111 |
| 4,788,221 | 11/1988 | Kagatani et al. | 514/808 |
| 5,002,771 | 3/1991 | Purkaystha et al. | 424/433 |
| 5,026,825 | 6/1991 | Grebow et al. | 530/307 |
| 5,393,738 | 2/1995 | Vonderscher et al. | 514/12 |
| 5,440,012 | 8/1995 | Takei et al. | 530/307 |

FOREIGN PATENT DOCUMENTS

| | | |
|---|---|---|
| 193372 | 9/1986 | European Pat. Off. . |
| 302772 | 2/1989 | European Pat. Off. . |
| 326151 | 8/1989 | European Pat. Off. . |
| 358234 | 3/1990 | European Pat. Off. . |
| 375885 | 7/1990 | European Pat. Off. . |
| 399781 | 11/1990 | European Pat. Off. . |
| 3335086 | 5/1984 | Germany . |
| 61-126014 | 6/1986 | Japan . |
| 2092002 | 8/1982 | United Kingdom . |
| 2142335 | 1/1985 | United Kingdom . |

OTHER PUBLICATIONS

European Search Report; EP 91 31 1176 dated Mar. 24, 1992.

Chem. Abs. 112(22) #204711y; Yamamoto et al; Calcitonin containing liquid pharmaceutical compositions for nasal applications.

Yamamoto et al., Chemical Abstracts, vol. 112, No. 22, Ab No:204711y, pp. 399, May 28, 1990.

*Primary Examiner*—Avis M. Davenport
*Attorney, Agent, or Firm*—Marla J. Mathias; Irving M. Fishman; Karen G. Kaiser

[57] ABSTRACT

A stable aqueous solution of human calcitonin (hCT) which remains free of hCT fibrils for at least 24 hours at 25° C. which comprises water, hCT and a cellulose derivative and/or an acid, the type of acid and the amount of acid being so chosen as to achieve said stability in the absence of a salt or a buffer.

7 Claims, No Drawings

STABLE CALCITONIN PHARMACEUTICAL COMPOSITIONS

This is a continuation of Ser. No. 08/073,646, filed Jun. 8, 1993, abandoned, which is a continuation of Ser. No. 09/805,252, filed Dec. 9, 1991, abandoned.

The present invention relates to stable compositions of human calcitonin (hCT), and in particular to stable aqueous solutions of hCT.

Calcitonin is a 32 amino acid polypeptide hormone secreted by the parafollicular cells of the thyroid gland in mammals and by the ultimobranchial gland of birds and fish. It is a potent drug for the treatment of Paget's disease, some aspects of hypercalcaemia, and for postmenopausal osteoporosis. Calcitonins of different origins, mainly salmon, pig, eel, and human are currently used therapeutically.

Human calcitonin, although considered less potent and thus required at higher concentrations or doses than salmon calcitonin, has the advantage of not generating neutralizing antibodies after prolonged administration as the salmon calcitonin does (Grauer et al. 1990, J. Bone Min. Res. 5, 387–391, Levy et at. 1988, J. Clin. Endocrinol. Metab. 67,541–545 and the references therein).

In physiological saline solutions or buffers, human calcitonin is not stable, it precipitates and forms fibrils. Due to the fibril formation phenomenon, the injectable dosage form of human calcitonin is made up when required by mixing hCT powder and the aqueous solution prior to injection. This procedure is not required for salmon calcitonin which is provided in solution.

The present invention describes the preparation of long-term stable liquid formulations of human calcitonin.

We have now found that stable aqueous solutions of hCT can be made in acidic media in the absence of salts and buffering agents, and/or in the presence of a cellulose derivative.

Accordingly the present invention provides a stable aqueous solution of human calcitonin (hCT) which remains free of hCT fibrils for at least 24 hours at 25° C. which comprises water, hCT and a cellulose derivative and/or an acid, the type of acid and the amount of acid being so chosen as to achieve said stability in the absence of a salt or a buffer.

The hCT used may be synthetic or it may be produced by recombinant DNA technology.

Suitable cellulose derivatives include methyl celluloses, hydroxypropyl methyl celluloses and dextrans, preferably a methyl cellulose.

The concentration of cellulose derivative may be from 0.1 to 2% by weight, preferably 0.2 to 1% by weight.

Suitable acids include organic and inorganic acids. Organic acids may be monocarboxylic, dicarboxylic, tetra-carboxylic, hydroxycarboxylic acids or phenols. Not all acids within a particular class of acid work and no strict correlation has been found between acid type and its ability to stabilise hCT.

The ability of an acid to produce a stable solution can be readily determined by making up a solution and storing it for 24 hours at 25° C. If, after this time the solution remains clear, the acid has stabilised the solution and is one which is suitable for use in an aqueous solution according to the present invention.

Examples of acids which form stable solutions are formic acid, acetic acid, ascorbic acid, hydrochloric acid, malonic acid, glutaric acid, adipic acid, citric acid, L-α-tartaric acid, DL-tartaric acid, ethylene - diamine tetraacetic acid and phenol.

Examples of acids which do not form stable solutions are aspartic acid, D-glutamic acid, sulphuric acid, gluconic acid and maleic acid.

The degree of stability achieved depends on the acid used and its concentration, the concentration of hCT and the storage temperature. In general the higher the concentration of hCT and the higher the storage temperature, the shorter the time before precipitation occurs. In the case of the concentration of acid, more dilute acid in general improves the stability.

The concentration of acid may be up to 1% by weight or less and preferably 0.0001 to 0.01%.

In general 0.001% acid produced better stabilising conditions than 1% acid. Overall, the best case was found to be 0.001% acetic acid.

The concentration of hCT may be up to 50 mg/ml. Preferred ranges are from 3 to 10 mg/ml for nasal or oral solutions and from 0.5 to 3 mg/ml for injectable solutions.

The stability of the solution is dependent on the concentration. We have found a linear correlation between the natural logarithm of fibrillation time and the natural logarithm of hCT concentration at a given temperature. From measurements on hCT solutions with concentrations up to 100 mg/ml hCT and using the ln/ln plot, stability of more than 5 years at 4° C. is predicted for solutions with 5–9 mg/ml hCT in 0.001% acetic acid.

The solution may be made by adding an aqueous solution of the cellulose derivative and/or acid to hCT powder and then stirring to dissolve. Any suitable stirrer may be used, e.g. a vortex mixer. If both a cellulose derivative and an acid are used it is preferred to dissolve the hCT powder in an aqueous solution of the acid and then add an aqueous solution of the cellulose derivative.

The stirring is preferably carried out under an inert gas atmosphere, such as nitrogen or argon, and the resulting solution is preferably degassed under vacuum. The inert gas atmosphere and degassing both help to prolong the stability of the solution. After preparation the solution may be stored in glass or plastics containers.

After preparation of the hCT solution, it may be mixed with solutions containing viscosity-increasing swelling agents and/or sugars and/or other additives. Suitable compounds which do not diminish the stability include sugars such as sucrose, fructose, glucose, lactose, mannitol and trehalose, ethanol, bovine serum albumin, lysozyme or high glucose concentration, and preservatives such as benzalkonium chloride, benzethonium chloride, tertiary ammonium salts and chlorhexidine diacetate. Examples of tertiary ammonium salts include hexadecyltrimethyl ammonium bromide, desqualamine chloride, methylbenzethonium chloride and benzyldimethylhexadecyl ammonium chloride.

Some of the additives, particularly preservatives such as benzethonium chloride improve the stability of the solutions to which they are added. Particularly good results have been obtained using a mixture of 0.5% methyl cellulose with 0.01% benzethonium chloride, and a mixture of 0.5% methyl cellulose, 0.01% benzethonium chloride and 0.001% acetic acid. Stability predictions using the ln/ln plot described above for these solutions at a concentration of 3.3 mg/ml hCT are 95 and 111 years respectively.

The amount of additives used can vary and may depend on the intended use. For example for nasal or oral solutions, 0.5 to 1% by weight of additive may be used. In the case of injectable solutions, sugars only would be used as the additive, usually in amounts of 0.5 to 1% by weight.

It should be noted that buffers and salts containing metal ions strongly induce the fibril formation process and should be avoided. The suitability of any additive can be readily ascertained in the same way as the suitability of an acid can be ascertained.

The solutions of the invention are stable not only with regard to fibrillation but also with regard to chemical decomposition of the hCT.

The stable hCT solutions of the invention may be administered orally, nasally or by injection.

The invention is illustrated by the following Examples, in which all percentages are by weight.

EXAMPLE 1

Dilute acetic acid at various concentrations is added to hCT powder and solubilisation is performed using a vortex mixer for 1–2 minutes. The resulting solutions containing 5 mg/ml hCT at acetic acid concentrations of 0.0001%, 0.001%, 0.01%, 0.1% and 1.0% are stable and perfectly clear after 8 months.

In vivo experiments show that fresh hCT solutions and solutions stored for 40 days have similar biological activity.

Absorption spectra and HPLC experiments show no change in hCT properties due to storing hCT in aqueous solutions.

EXAMPLE 2

Solutions are prepared by the method of Example 1 with or without other additives. The additives used and the resulting stability are shown in Table I below. The three negative results in the stability test show that while stable solutions can be produced with the additives concerned, the concentration should be controlled so as not to ensure instability.

TABLE I

Systems studied for long-time hCT stability
Conditions of stability: Aqueous suspension
of hCT, 5 mg/ml hCT, 4° C., more than 31 days.

| Nr. | AQUEOUS SUSPENSION | ADDITIVE | STABILITY |
|---|---|---|---|
| 1 | 0.100% Acetic acid (AA) | — | + |
| 2 | 0.080% AA | — | + |
| 3 | 0.070% AA | — | + |
| 3 | 0.060% AA | — | + |
| 4 | 0.050% AA | — | + |
| 5 | 0.030% AA | — | + |
| 6 | 0.010% AA | — | + |
| 7 | 0.005% AA | — | + |
| 8 | 0.001% AA | — | + |
| 9 | 0.100% AA | 2% Sucrose | + |
| 10 | 0.010% AA | 2% Sucrose | + |
| 11 | 0.001% AA | 2% Sucrose | + |
| 12 | 0.100% AA | 4% Sucrose | + |
| 13 | 0.010% AA | 4% Sucrose | + |
| 14 | 0.001% AA | 4% Sucrose | + |
| 15 | 0.100% AA | 2% Fructose | + |
| 16 | 0.010% AA | 2% Fructose | + |
| 17 | 0.001% AA | 2% Fructose | + |
| 18 | 0.100% AA | 4% Fructose | + |
| 19 | 0.010% AA | 4% Fructose | + |
| 20 | 0.001% AA | 4% Fructose | + |
| 21 | 0.100% AA | 2% Glucose | + |
| 22 | 0.010% AA | 2% Glucose | + |
| 23 | 0.001% AA | 2% Glucose | + |
| 24 | 0.100% AA | 4% Glucose | + |
| 25 | 0.010% AA | 4% Glucose | + |
| 26 | 0.001% AA | 4% Glucose | + |
| 27 | 0.100% AA | 2% Lactose | + |
| 28 | 0.010% AA | 2% Lactose | + |
| 29 | 0.001% AA | 2% Lactose | + |
| 30 | 0.100% AA | 4% Lactose | + |
| 31 | 0.010% AA | 4% Lactose | + |
| 32 | 0.001% AA | 4% Lactose | + |
| 33 | 0.100% AA | 2% Manitol | + |
| 34 | 0.010% AA | 2% Manitol | + |
| 35 | 0.001% AA | 2% Manitol | + |
| 36 | 0.100% AA | 4% Manitol | + |
| 37 | 0.010% AA | 4% Manitol | + |
| 38 | 0.001% AA | 4% Manitol | + |
| 39 | 0.100% AA | 2% Trehalose | + |
| 40 | 0.010% AA | 2% Trehalose | + |
| 41 | 0.001% AA | 2% Trehalose | + |
| 42 | 0.100% AA | 4% Trehalose | + |
| 43 | 0.010% AA | 4% Trehalose | + |
| 44 | 0.001% AA | 4% Trehalose | + |
| 45 | 0.001% AA, 0.100% Ethanol | — | + |
| 46 | 0.001% AA, 0.100% Ethanol | 4% Mannitol | + |
| 47 | 0.001% AA, 0.010% Ethanol | — | + |
| 48 | 0.001% AA, 0.010% Ethanol | 4% Mannitol | + |
| 49 | 0.001% AA | 100 mg/ml BSA (1:1) | − |
| 50 | 0.001% AA | 50 mg/ml BSA (2:1) | − |
| 51 | 0.001% AA | 10 mg/ml BSA (10:1) | + |
| 52 | 0.001% AA | 1 mg/ml BSA (100:1) | + |
| 53 | 0.001% AA | 23 mg/ml Lysozyme (1:1) | − |
| 54 | 0.001% AA | 11.5 mg/ml Lysozyme (2:1) | + |
| 55 | 0.001% AA | 2.3 mg/ml Lysozyme (10:1) | + |
| 56 | 0.001% AA | 0.23 mg/ml Lysozyme (100:1) | + |
| 57 | 0.010% AA | 10% Glucose | + |
| 58 | 0.010% AA | 20% Glucose | + |
| 59 | 0.010% AA | 30% Glucose | + |
| 60 | 0.010% AA | 40% Glucose | + |

EXAMPLE 3

Example 1 is repeated except that the solutions also contain 0.5% hydroxypropylmethylcellulose. The solutions are stable for more than 3.5 months at 4° C., 22° C., and 37° C. in the dark or in daylight. The solutions are also stable against fibril formulation after 24 hours at 47° C. in a SUNTEST accelerated light exposure machine.

EXAMPLE 4

Example 1 is repeated except that the acetic acid is replaced by the following acids: ascorbic acid, formic acid, hydrochloric acid, succinic acid, L-glutamic acid, malonic acid, glutaric acid, adipic acid, citric acid, L-2-tartaric acid and DL-tartaric acid. In each case the solution is stable for over 4 days.

EXAMPLE 5

Solutions of hCT are made using different concentrations of methyl cellulose (MC) and hydroxypropyl methyl cellulose (HPMC) with and without 0.01% benzethonium chloride (BTC), in one case also with 0.001% acetic acid (AA) and in one case using 0.5% dextran (D). The extrapolated time of fibrillation in years is given for hCT concentration of 3.3 mg/ml and 6.6 mg/ml. The formulations and results are shown in Table II.

TABLE II

| No. | Cellulose Derivative | BTC | AA | Time of Fibrillation (years) | |
|---|---|---|---|---|---|
| | | | | 3.3 mg/ml | 6.6 mg/ml |
| 1 | 0.5% HPMC | — | — | 17.5 | 1.5 |
| 2 | 0.5% HPMC | 0.01% | — | 22.2 | 2 |
| 3 | 0.5% MC | — | — | 7.2 | 0.9 |
| 4 | 0.5% MC | 0.01% | — | 9.5 | 7.5 |
| 5 | 0.5% MC | 0.01% | 0.001% | 111 | 7.5 |
| 6 | 1% MC | — | — | 7.8 | 1 |
| 7 | 1% MC | 0.01% | — | 14.7 | 1.67 |
| 8 | 0.34% MC | 0.01% | — | 16.5 | 1.9 |
| 9 | 0.34% HPMC | 0.01% | — | 7.8 | 1 |
| 10 | 0.2% MC | 0.01% | — | 11.2 | 1.3 |
| 11 | 2% HPMC | 0.01% | — | 8.7 | 0.85 |
| 12 | 0.5% D | — | — | 0.5 | 26 days |

EXAMPLE 6

A solution of hCT is made containing 3.3 mg/ml hCT, 0.5% methyl cellulose, 0.02% benzethonium chloride and 0.001% acetic acid. Chemical stability tests (Roger's test) predicted only 0.02% chemical decomposition of the hCT in 5 years for storage at 10° C.

We claim:

1. A stable aqueous solution of human calcitonin (hCT) which remains free of hCT fibrils for at least 24 hours at 25° C. which comprises water, hCT and at least one compound selected from the group consisting of formic acid, acetic acid, ascorbic acid, hydrochloric acid, succinic acid, L-glutamic acid, malonic acid, glutaric acid, adipic acid, citric acid, L-a-tartaric acid, DL-tartaric acid, ethylene diamine tetraacetic acid, and phenol, the concentration of acid being from 0.0001% to 0.01% by weight and in the absence of a metal salt or buffer.

2. A solution as claimed in claim 1 which comprises 0.5 to 10 mg/ml hCT.

3. A solution as claimed in claim 1 which further comprises at least one additive selected from the group consisting of a viscosity increasing swelling agent and a sugar.

4. A solution as claimed in claim 3 which comprises at least one additive selected from the group consisting of sucrose, fructose, glucose, lactose, mannitol, trehalose, ethanol, bovine serum albumin, lysozyme, benzalkonium chloride, benzethonium chloride, a tertiary ammonium salt and chlorhexidine diacetate.

5. A method for making a stable aqueous solution of hCT as claimed in claim 1 which comprises adding an aqueous solution of the acid to powder hCT and then stirring to dissolve the powder.

6. A method as claimed in claim 5 in which the stirring is carried out under an inert gas atmosphere.

7. A method as claimed in claim 5 in which the resulting solution is degassed under vacuum.

* * * * *